(12) United States Patent
Razavi

(10) Patent No.: US 7,569,713 B2
(45) Date of Patent: Aug. 4, 2009

(54) HYDROGENATED CATALYST
(75) Inventor: Abbas Razavi, Mons (BE)
(73) Assignee: Total Petrochemicals Research Feluy, Feluy (BE)
( * ) Notice: Subject to any disclaimer, the term of this patent is extended or adjusted under 35 U.S.C. 154(b) by 0 days.
(21) Appl. No.: 10/547,954
(22) PCT Filed: Mar. 2, 2004
(86) PCT No.: PCT/EP2004/002146

§ 371 (c)(1),
(2), (4) Date: Nov. 3, 2006

(87) PCT Pub. No.: WO2004/078798

PCT Pub. Date: Sep. 16, 2004

(65) Prior Publication Data
US 2007/0155619 A1 Jul. 5, 2007

(30) Foreign Application Priority Data
Mar. 6, 2003 (EP) .................................. 03075653

(51) Int. Cl.
C07F 17/00 (2006.01)
C07F 7/08 (2006.01)
C08F 4/64 (2006.01)
C08F 4/76 (2006.01)
(52) U.S. Cl. ............................. 556/53; 556/52; 556/51; 556/11; 556/12; 526/941; 526/160; 526/170; 526/943; 502/103
(58) Field of Classification Search .................. 556/51, 556/53, 11, 12, 52; 502/103, 152; 526/170, 526/160, 943, 941, 126
See application file for complete search history.

(56) References Cited
U.S. PATENT DOCUMENTS
4,357,337 A * 11/1982 Dubroeucq et al. ......... 514/319
(Continued)

FOREIGN PATENT DOCUMENTS
DE 4125135 A1 2/1993
(Continued)

OTHER PUBLICATIONS
Mengele, W. et al. Organometallics 1993, 12, 1931-1935.*
(Continued)

Primary Examiner—David Wu
Assistant Examiner—Rip A. Lee
(74) Attorney, Agent, or Firm—Diane L. Kilpatrick-Lee

(57) ABSTRACT

The invention discloses a method for making a hydrogenated metallocene catalyst component comprising the steps of: 1. Providing a compound comprising at least one aromatic group; 2. Hydrogenating the at least one aromatic group in the presence of hydrogen and a hydrogenation catalyst to form a hydrogenated compound; and 3. Forming a metallocene catalyst component from the hydrogenated compound from step 2.

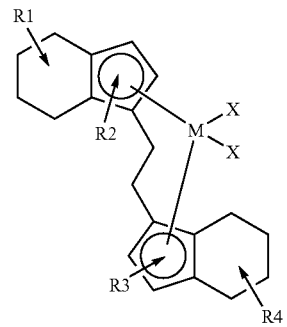

13 Claims, 2 Drawing Sheets

U.S. PATENT DOCUMENTS

Figure 1:
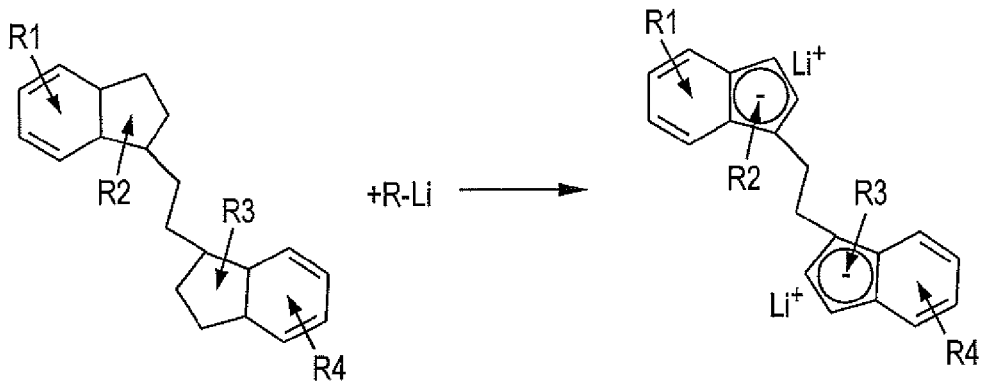
Figure 1:
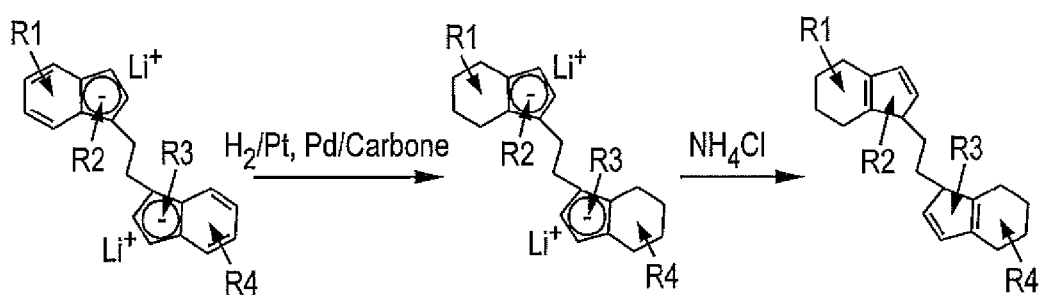
Figure 1:
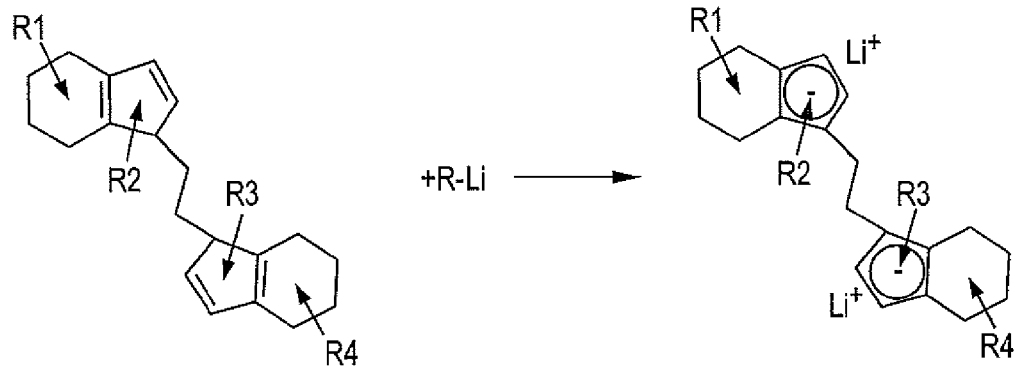
Figure 1:
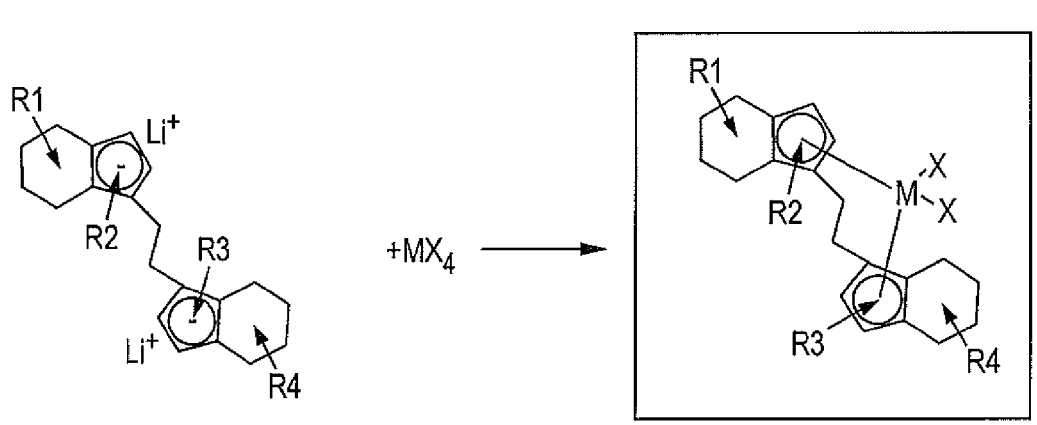

| | | | |
|---|---|---|---|
| 5,004,820 A * | 4/1991 | Buchwald et al. | 556/53 |
| 5,017,714 A | 5/1991 | Welborn, Jr. | |
| 5,120,867 A | 6/1992 | Welborn, Jr. | |
| 5,276,208 A * | 1/1994 | Winter et al. | 556/53 |
| 5,314,973 A | 5/1994 | Welborn et al. | |
| 5,496,902 A * | 3/1996 | Evertz et al. | 526/127 |
| 5,594,081 A * | 1/1997 | Uchino et al. | 526/127 |
| 5,705,579 A * | 1/1998 | Hawley et al. | 526/160 |
| 5,883,275 A * | 3/1999 | Bingel et al. | 556/9 |
| 5,929,266 A | 7/1999 | Jones et al. | |
| 5,990,331 A * | 11/1999 | Winter et al. | 556/9 |
| 6,084,043 A | 7/2000 | Sugano et al. | |
| 6,153,549 A * | 11/2000 | Hubscher et al. | 502/103 |
| 6,437,161 B1 * | 8/2002 | Mihan et al. | 556/11 |
| 6,458,982 B1 * | 10/2002 | Schottek et al. | 556/53 |
| 6,541,584 B1 * | 4/2003 | Resconi | 526/160 |
| 6,765,103 B2 * | 7/2004 | Giese et al. | 556/11 |
| 6,861,543 B2 | 3/2005 | Biagini et al. | |
| 2004/0167017 A1 | 8/2004 | Biagini et al. | |

FOREIGN PATENT DOCUMENTS

| | | |
|---|---|---|
| EP | 0344887 A3 | 12/1989 |
| EP | 0485821 B1 | 5/1992 |
| EP | 0697418 B1 | 2/1996 |
| JP | 01-165532 A1 | 6/1989 |

OTHER PUBLICATIONS

Kelly, P. et al. J. Organic Chem. 2003, 68, 8447-8452.*
Halterman, R. J. Organomet. Chem. 2000, 604, 12-19.*

* cited by examiner

STEP 1

STEP 2

STEP 3

STEP 4

STEP 1

STEP 2

STEP 3

STEP 4

HYDROGENATED CATALYST

The present invention relates to a method for making a hydrogenated catalyst component and to a hydrogenated metallocene catalyst component made by the method and to uses thereof.

A C2-symmetric metallocene catalyst component can appear in two stereo-isomeric forms: a racemic form and a meso form. A stereospecific catalyst is used to prepare stereoregular polyolefins. It is generally known that the racemic form induces a reproducible orientation of incoming monomers when the catalyst component is used in an olefin polymerisation reaction. This is desirable for producing an isotactic polyolefin.

Attempts have been made either to avoid the production of the meso isomer or to separate the desirable racemic isomer from the meso isomer, but the separation step is costly and it has been observed that after purification the meso isomer is reintroduced in the system under the effect of light or heat. Hydrogenation of the catalyst component avoids the formation of the meso isomer and/or its "re-formation" under the effect of light or heat. As such, a hydrogenated metallocene catalyst component is known to be useful in olefin polymerisation.

However, aromatic compounds are notoriously difficult substrates to hydrogenate.

In the specific context of bridged bis-indenyl-based metallocenes it is known in the art that these give rise to the formation of two isomeric metallocenes (racemic and meso) with different catalytic properties. The non-stereo specific meso component contributes to the formation of an undesirable low molecular weight atactic polymer fraction whereas the racemic component produces a highly stereoregular polymer fraction. In addition, starting from pure racemic ingredients, heat and light induce the transformation of part of the racemic precatalyst into the meso isomer, thereby leading to the formation of lower molecular weight "solubles" after activation and during the polymerisation. This is particularly detrimental in the production of copolymer of polyethylene/polypropylene.

It has been observed that hydrogenation of the indenyl rings reduces the production of the meso isomer during the final steps of the metallocene synthesis, but so far hydrogenation has been carried out only on the final catalyst and has been successful only for unsubstituted bis-indenyl components and with somewhat successful on mono-substituted bis-indenyl components.

J. Organomet. Chem. (1982), 282, 233-247 describes the synthesis of ethylene-bis(4,5,6,7-tetrahydro-1-indenyl)-titanium dichloride. This is made by hydrogenation of ethylene-bis(indenyl)titanium using either a palladium-on-charcoal hydrogenation catalyst or a $PtO_2$ hydrogenation catalyst. This hydrogenation reaction is said, in principle to give the chiral compound in sufficiently pure form. However, it is said that, in practice, the need for chromatographic separations and the loss of a major product portion in form of the achiral meso-isomer are impediments.

EP 0344887 is concerned with a chiral silicon-bridged metallocene catalyst that polymerises α-olefins to high isotacticity with a minimum of inversions at high rates of catalyst activity. In Example 1, the compound 1,1'-dimethylsilanylene bridged bis(indenyl) zirconium dichloride was prepared. Further, the tetrahydroindenyl derivative of this compound was prepared by adding methylene chloride and platinum black or platinum (IV) oxide. Following hydrogenation, the insoluble racemic isomer was filtered off and crystallised. Similarly as for Example 1, in Example 7, tetramethyldisiloxane bridged bis(tetrahydroindenyl) zirconium dichloride was prepared.

In summary of the state of the art as outlined above, U.S. Pat. No. 5,883,275 acknowledges that the synthesis of hydrogenated or partially hydrogenated metallocenes generally starts from the corresponding metallocenes having aromatic ligands. It further is stated that the known synthetic procedures for hydrogenating the aromatic ligand skeleton of metallocenes in principle all follow the same route. The metallocene is dissolved or suspended in dichloromethane and hydrogenated in the presence of platinum back or platinum dioxide under a high pressure of oxygen. However, U.S. Pat. No. 5,883,275 alleges some disadvantages of these known procedures.

As such, U.S. Pat. No. 5,883,275 proposes an alternative method for synthesising hydrogenated metallocene. As with previously known methods, the procedure of U.S. Pat. No. 5,883,275 also starts from the corresponding metallocene having aromatic ligands. However, a new method for hydrogenation is proposed insofar as the metallocene to be treated with hydrogen in the presence of a hydrogenation catalyst is in a non-halogenated solvent. This non-halogenated solvent is essential for achieving the advantages set out in column 6 of U.S. Pat. No. 5,883,275.

In J. Organomet. Chem., 604 (2000), 12-19, it also is acknowledged that the hydrogenation of bis(indenyl) zirconium dichloride to give the corresponding bis(tetrahydroindenyl) zirconium dichloride has been reported. However, it is further acknowledged that the ability to hydrogenate the six-membered ring in indenyl metal complexes is not general. This document reports a different approach for synthesising bis(tetrahydroindenyl) lanthanum chlorides directly from "pre-reduced" bis(tetrahydroindenyl) ligands. The synthesis of 2-methyl-4,5,6,7-tetrahydroindenyl lithium is shown in scheme 1 of this document. The synthesis of silyl-bridged bis(tetrahydroindene) is reported in Scheme 2.

In view of the above, it will be understood that there is a need for further, and preferably improved, methods for making a hydrogenated metallocene catalyst component, which catalyst component preferably polymerises α-olefins to high isotacticity.

Accordingly, a first aspect of the present invention provides a method for making a hydrogenated metallocene catalyst component comprising the steps of:
1. providing a compound comprising at least one aromatic group;
2. hydrogenating the at least one aromatic group in the presence of hydrogen and a hydrogenation catalyst to form a hydrogenated compound; and
3. forming a metallocene catalyst component from the hydrogenated compound from step 2.

A second aspect of the present invention provides, a hydrogenated metallocene catalyst component preparable by the method as defined in the first aspect of the present invention.

A third aspect of the present invention provides, a catalyst system comprising a catalyst component as defined in the second aspect of the present invention and further comprising an aluminium- or boron-containing activating agent capable of activating the catalyst component.

A fourth aspect of the present invention provides a method for producing a polyolefin, which method comprises polymerising an olefin monomer in the presence of a catalyst component or catalyst system as defined in relation to the second or third aspects of the present invention.

A fifth aspect of the present invention provides a polyolefin, obtainable by the method as defined in relation to the fourth aspect of the present invention.

Preferably, the hydrogenated metallocene catalyst component produced by the method according to the first aspect of the present invention is C2-symmetric. As such, the catalyst component will be formed as a part of a mixture of the racemic and meso forms.

In the method according to the first aspect, hydrogenating in step 2 is to form a hydrogenated compound corresponding to the compound provided in step 1. Any substituents present on the compound provided in step 1 are retained during steps 2 and 3.

Preferably, the compound provided in step 1 is substituted, more preferably, at least disubstituted.

Step 2 preferably includes a step of dissolving or suspending the compound from step 1 in a halogenated solvent, prior to hydrogenating in step 2. More preferably, the halogenated solvent is a chlorinated solvent, most preferably dichloromethane.

Further, the hydrogenation catalyst in step 2 preferably is platinum black or platinum dioxide.

Hydrogenating in step 2 preferably is carried out under high pressure of hydrogen ranging from 1 to 100 bar, preferably from 50 to 100 bar.

Referring now to step 3, typically this step comprises complexing the hydrogenated compound from step 2 with a metal atom to form the metallocene catalyst component. The hydrogenated compound from step 2 is or forms a ligand, coordinated to the central metal atom in the metallocene catalyst compound. To this end, step 3 preferably includes the steps of:

(a) deprotonating the hydrogenated compound from step 2 to produce a salt;
(b) reacting the salt from step (a) with a Group IIIB, IVB, VB, or IVB metal compound or a vanadium compound to form the metallocene catalyst component.

Preferably, step (a) uses alkyl lithium to deprotonate the hydrogenated compound to produce a dilithium salt.

Also preferably, in step (b) the metal compound is a halide, preferably a Group IVB metal tetrahalide. The preferred solvent in step (b) is tetrahydrofuran (THF).

Typically, the metallocene catalyst component produced in step 3 will form part of a mixture of diastereoisomeric metallocene catalyst components. In this case, the method optionally may include a step 4 of purifying the mixture to isolate the racemic isomer. Purification is carried out by fractionated crystallisation.

The hydrogenated metallocene catalyst component produced by the method according to the first aspect of the present invention may be bridged or unbridged. In a first embodiment where the product metallocene catalyst component is unbridged, the compound provided in step 1 preferably is indene, more preferably substituted indene, most preferably 2,4-disubstituted indene. The product of step 2 thus will be tetrahydroindene or, more preferably a substituted tetrahydroindene, most preferably a 2,4-disubstituted version thereof. Step 3 then would comprise a step of complexing the tetrahydroindene to a metal to form the metallocene catalyst component.

In a second embodiment, the hydrogenated metallocene catalyst component produced by the method according to the first aspect of the present invention is bridged.

The type of bridge present is not itself particularly limited. Typically, the bridging group comprises an alkylidene group having 1 to 20 carbon atoms, a germanium group (e.g. a dialkyl germanium group), a silicon group (e.g. a dialkyl silicon group), a siloxane group (e.g. a dialkyl siloxane group), an alkyl phosphine group or an amine group. Preferably, the bridging group is $Me_2C$, $Ph_2C$, ethylenyl, or $Me_2Si$.

It is particularly preferred that the catalyst comprises a $Me_2C$, $Ph_2C$ or $Me_2Si$ bridging group.

Two possibilities for forming a bridged catalyst component in accordance with the first aspect of the present invention will be described.

The first possibility is summarised in FIG. 1 that describes graphically the four steps leading to the final substituted hydrogenated bis-indenyl.

According to the first possibility, a "bridged" compound L-R"-L' is provided in step 1 wherein the compound comprises groups L and L', each comprising an aromatic group linked by a bridging group (R"). Such a compound may be prepared by reacting salts of the L and L' groups with a bridging agent comprising the bridging group (R"). L and L' may be the same or different. Preferably, L and L' are the same.

Preferably, the compound provided in step 1 is a bridged bis(indene). The bridged bis(indene) may be substituted or unsubstituted but preferably is substituted, more preferably 2,4 disubstituted.

Taking the example where the product hydrogenated metallocene catalyst component has a bridged bis(indenyl) ligand, according to the first possibility, the compound provided in step 1 is bridged bis (indene). Step 1 may include a step of forming the bridged bis(indene) by reacting a salt of indene with a dihaloethane, preferably dibromoethane, or dihalodialkylsilane bridging agent.

Preferably, a salt as referred to above is a Group 1A salt, preferably a lithium salt.

Figure 2:
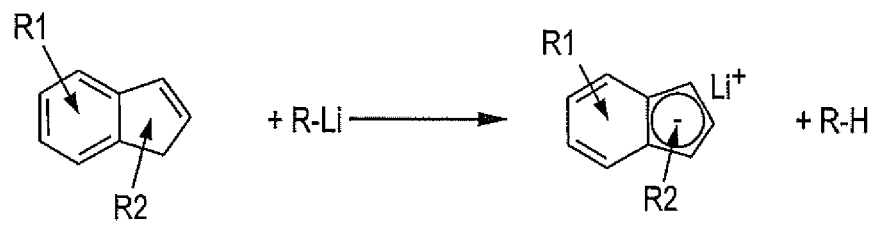
Figure 2:
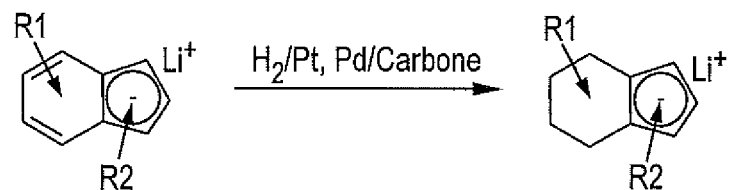
Figure 2:
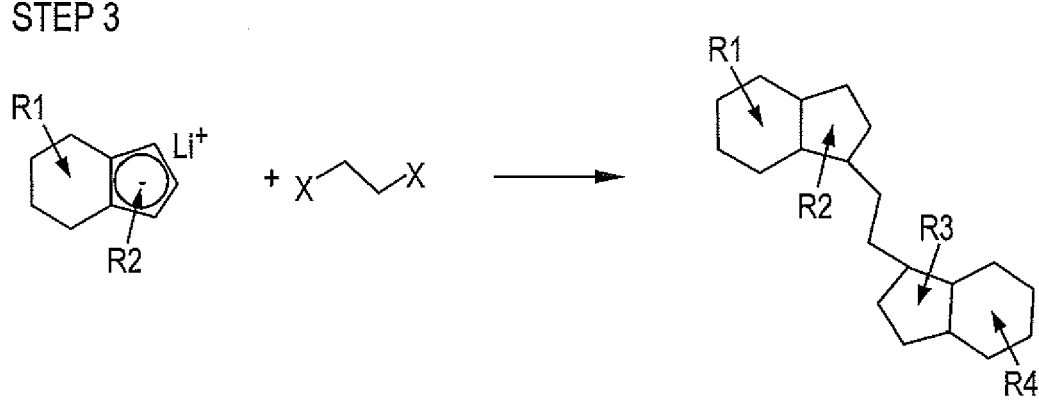
Figure 2:
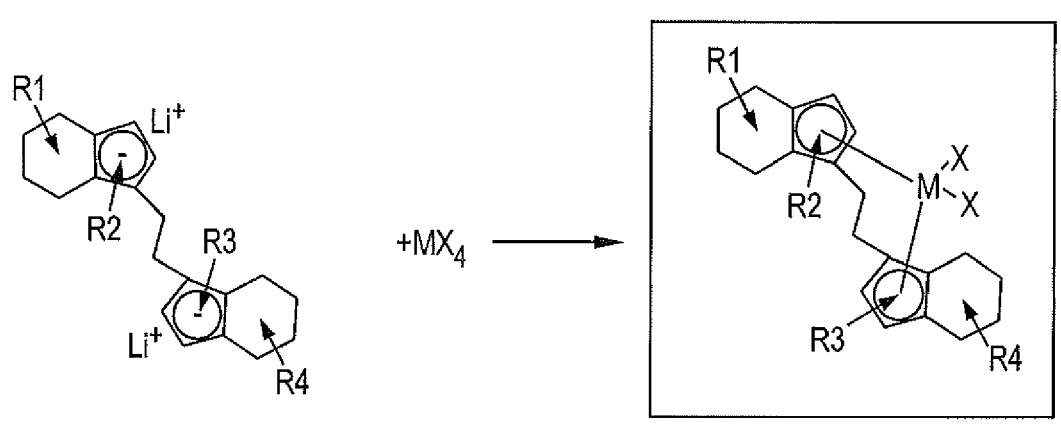

The second possibility is summarised in FIG. 2 that describes graphically the four steps leading to the final substituted hydrogenated bis-indenyl.

According to the second possibility, the compound provided in step 1 is converted into a bridged compound after hydrogenating in step 2. In this case, the compound provided in step 1 will be an unbridged salt (salt of L, salt of L'), preferably a Group 1A salt, more preferably a lithium salt. Again, the compound (salt of L, salt of L') may be substituted or unsubstituted. The compound is hydrogenated in step 2 and then reacted in step 3 with a bridging agent as defined above to form the bridged compound, prior to forming the metallocene catalyst component. Preferably, the bridging agent is a dihaloethane, preferably dibromoethane, or a dihalodialkylsilane bridging agent.

L and L' may be the same or different. Preferably, L and L' are the same.

Again, taking the example where the product hydrogenated metallocene catalyst component has a bridged bis(indenyl), ligand, according to the second possibility, the product of step 2 will be a 4,5,6,7-tetrahydroindene salt or a substituted version thereof. Preferably, the 4,5,6,7-tetrahydroindene salt is substituted, more preferably 2,4 disubstituted. This is then reacted with a bridging agent to produce a substituted or unsubstituted bridged bis(tetrahydroindenyl).

Turning to the second aspect of the present invention, preferably, the metallocene catalyst component has formula (I):

$$(THI\text{-}R_m)_2R''_nMQ_p \qquad (I)$$

wherein each THI is the same or different and is a tetrahydroindenyl group; each R is the same or different and is a hydrocarbyl group having from 1-20 carbon atoms; m is an integer from 2 to 7; R" is a structural bridge imparting stereorigidity to the catalyst; n is 0 or 1; M is a metal atom from Group IIIB, IVB, VB or VIB or is vanadium; each Q is a hydrocarbon having from 1-20 carbon atoms or is a halogen and p is the valence of M minus 2.

Any of the positions on the tetrahydroindenyl group may comprise a substituent in place of a hydrogen atom. Thus, whilst each substituted THI group may be a tetrahydroindenyl group with the substituent present on the five-membered ring, it may alternatively be a group that comprises the same pattern of saturation as tetrahydroindenyl, but in which one or more of the hydrogen atoms on the six-membered ring has been replaced. Alternatively, and preferably, the substituents may be present on both the five-membered and the six-membered ring.

Each catalyst component comprises two (THI-$R_m$) groups. The two groups may be different. However, it is preferred that the two (THI-$R_m$) groups of the catalyst component are the same. Typically the two (THI-$R_m$) groups are asymmetric and the hydrogenated catalyst component is C2-symmetric.

Preferably, at least one of the tetrahydroindenyl groups is substituted. More preferably, at least one of the tetrahydroindenyl groups is substituted at the 2-position and/or the 4-position. Even more preferably, in formula (I), at least one m is 2. Most preferably, at least one of the tetrahydroindenyl groups is substituted at both the 2-position and the 4-position. Preferably, R is an alkyl having from 1 to 7 carbon atoms.

Preferably, M in formula (I) is a metal atom from Group IVB and p is 2.

Referring to the third aspect of the present invention, suitable aluminium-containing activating agents comprise an alumoxane, an alkyl aluminium compound and/or a Lewis acid.

The alumoxanes that can be used in the present invention are well known and preferably comprise oligomeric linear and/or cyclic alkyl alumoxanes represented by the formula (A):

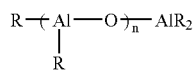
(A)

for oligomeric linear alumoxanes; and formula (B)

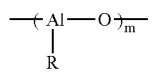
(B)

for oligomeric cyclic alumoxanes, wherein n is 1-40, preferably 10-20; m is 3-40, preferably 3-20; and R is a $C_1$-$C_8$ alkyl group, preferably methyl. Generally, in the preparation of alumoxanes from, for example, aluminium trimethyl and water, a mixture of linear and cyclic compounds is obtained.

The amount of alumoxane and metallocene usefully employed in the preparation of a solid support catalyst can vary over a wide range. Generally the aluminium to transition metal mole ratio is in the range between 1:1 and 100:1, preferably in the range 5:1 and 80:1 and more preferably in the range 5:1 and 50:1.

When Q in general formula (I) includes a alkyl group, preferred activating agents include hydroxy isobutylaluminium and metal aluminoxinates. These are particularly, preferred for metallocenes as described in Main Groups Chemistry, 1999, Vol. 3, pg. 53-57; Polyhedron 18 (1999) 2211-2218; and Organometallics 2001, 20, 460-467.

Suitable boron-containing activating agents may comprise a triphenylcarbenium boronate, such as tetrakis-pentafluorophenyl-borato-triphenylcarbenium as described in EP-A-0427696:

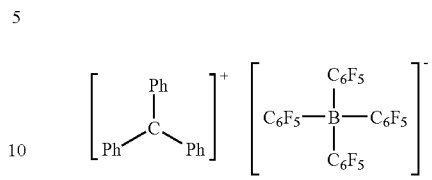

or those of the general formula below, as described in EP-A-0277004 (page 6, line 30 to page 7, line 7):

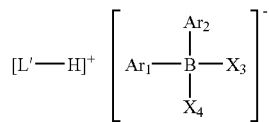

Referring now to the fourth aspect of the present invention, the olefin monomer preferably is ethylene or propylene.

The conditions under which the polymerising step is carried out are not especially limited.

Advantageously high polymerisation temperatures may be employed, such as from 50 to 120° C.

Typical polymerisation conditions in a slurry polymerisation are at a temperature of from 20-120° C., a pressure of from 0.1-5.6 MPa and a reaction time of from 10 mins to 4 hours.

The catalyst system of the present invention may be employed in any polymerisation method such as a slurry polymerisation, a solution polymerisation, or a gas phase polymerisation, provided that the required catalytic activity is not impaired. In a preferred embodiment of the present invention, the catalyst system is employed in a solution polymerisation process, which is homogeneous, or a slurry process, which is heterogeneous. In a solution process, typical solvents include hydrocarbons having 4-7 carbon atoms such as heptane, toluene or cyclohexane. In a slurry process it is necessary to immobilise the catalyst system on an inert support, particularly a porous solid support such as talc, inorganic oxides and resinous support materials such as polyolefin. Preferably, the support material is an inorganic oxide in its finely divided form.

Suitable inorganic oxide materials which are desirably employed in accordance with this invention include group IIA, IIIA, IVA, or IVB metal oxides such as silica, alumina and mixtures thereof. Other inorganic oxides that may be employed either alone or in combination with the silica, or alumina are magnesia, titania, zirconia, and the like. Other suitable support materials, however, can be employed, for example, finely divided functionalised polyolefins such as finely divided polyethylene.

Preferably, the support is a silica support having a surface area of from 100-1000 $m^2$/g, more preferably from 200-700 $m^2$/g, and a pore volume of from 0.5-4 ml/g, more preferably from 0.5-3 ml/g.

The order of addition of the catalyst component and activating agent to the support material can vary. In accordance with a preferred embodiment of the present invention, alumoxane dissolved in a suitable inert hydrocarbon solvent is added to the support material slurried in the same or other suitable hydrocarbon liquid and thereafter the catalyst component is added to the slurry.

Preferred solvents include mineral oils and the various hydrocarbons which are liquid at reaction temperature and which do not react with the individual ingredients. Illustrative examples of the useful solvents include the alkanes such as pentane, iso-pentane, hexane, heptane, octane and nonane; cycloalkanes such as cyclopentane and cyclohexane, and aromatics such as benzene, toluene, ethylbenzene and diethylbenzene.

Preferably the support material is slurried in toluene and the catalyst component and alumoxane are dissolved in toluene prior to addition to the support material.

The molecular weight of the polyolefin backbone formed in the method according to the fourth aspect is not especially limited. Typically, the backbone has a weight average molecular weight, such as of from 100,000 to 1,400,000. Preferably the molecular weight of the backbone is from 300,000 to 800,000.

The polyolefins prepared with the hydrogenated catalyst system of the present invention have less regio-defects and are more stereo-regular than those obtained with their non-hydrogenated counterpart.

Finally, a sixth aspect of the present invention provides the use of a catalyst component or catalyst system as defined in relation to the second or third aspects of the present invention for the preparation of a polyolefin. Preferably, use is for the preparation of a polyethylene or a polypropylene.

Unbridged substituted bis-tetrahydroindenyl catalyst components have successfully been employed for the homo- or co-polymerisation of ethylene.

What is claimed is:

1. A method for the preparation of a bridged hydrogenated metallocene catalyst component comprising:
   (a) providing a metallocene precursor having at least one aromatic group, wherein said metallocene precursor is a substituted or unsubstituted bridged bis(indenyl) salt;
   (b) contacting said metallocene precursor with hydrogen in the presence of a hydrogenation catalyst to hydrogenate said metallocene precursor component to form a hydrogenated metallocene precursor; and
   (c) thereafter forming a bridged hydrogenated metallocene catalyst component by reacting said hydrogenated metallocene precursor with a Group IIIB, IVB, VB or VIB metal compound.

2. The method of claim 1 comprising dispersing said metallocene precursor in a halogenated solvent and thereafter hydrogenating said metallocene precursor in accordance with subparagraph (b).

3. The method of claim 2 wherein said halogenated solvent is a chlorinated solvent.

4. The method of claim 3 wherein said chlorinated solvent is dichloromethane.

5. The method of claim 1 wherein said hydrogenation catalyst is platinum black or platinum dioxide.

6. The method of claim 1 wherein said metallocene precursor is a bridged bis(disubstituted indenyl) salt with substituents at the 2 and 4 positions.

7. A method for the preparation of a bridged hydrogenated metallocene catalyst component comprising:
   (a) providing a metallocene precursor having at least one aromatic group, wherein said metallocene precursor is a substituted or unsubstituted salt of indene;
   (b) contacting said metallocene precursor with hydrogen in the presence of a hydrogenation catalyst to hydrogenate said metallocene precursor component to form a hydrogenated metallocene precursor; and
   (c) thereafter forming a bridged metallocene catalyst component by:
      (i) reacting said hydrogenated metallocene precursor with a dihalo bridging agent to form a bridged compound;
      (ii) deprotonating said bridged compound to produce a salt thereof; and thereafter
      (iii) reacting said salt with a Group IIIB, IVB, VB or VIB metal compound to form said bridged hydrogenated metallocene catalyst component.

8. The method of claim 7 comprising dispersing said metallocene precursor in a halogenated solvent and thereafter hydrogenating said metallocene precursor in accordance with subparagraph (b).

9. The method of claim 8 wherein said halogenated solvent is a chlorinated solvent.

10. The method of claim 9 wherein said chlorinated solvent is dichloromethane.

11. The method of claim 7 wherein said bridging agent is dihaloethane or a dihalodialkylsilane.

12. The method of claim 11 wherein said bridging agent is dibromoethane.

13. The method of claim 7 wherein said hydrogenation catalyst is platinum black or platinum dioxide.

* * * * *